(12) United States Patent
Rushing

(10) Patent No.: US 6,791,485 B1
(45) Date of Patent: Sep. 14, 2004

(54) DIGITAL DENSITOMETER USING LIGHT-TO-FREQUENCY CONVERTER

(76) Inventor: Allen Joseph Rushing, 429 Tara La., Webster, NY (US) 14580

( * ) Notice: Subject to any disclaimer, the term of this patent is extended or adjusted under 35 U.S.C. 154(b) by 403 days.

(21) Appl. No.: 10/095,166

(22) Filed: Mar. 11, 2002

Related U.S. Application Data

(63) Continuation-in-part of application No. 09/543,094, filed on Apr. 3, 2000, now abandoned, and a continuation-in-part of application No. 09/873,465, filed on Jun. 4, 2001, now Pat. No. 6,671,052.

(51) Int. Cl.[7] .......................... H03M 1/18; G01N 21/00; H03L 7/08
(52) U.S. Cl. ............................... 341/139; 250/214 DC; 331/10
(58) Field of Search .................................. 341/138, 139; 250/214 DC, 214 AG; 331/10, 11, 14, 16, 18, 17, 23, 25; 327/156–160; 399/26, 31, 49, 51

(56) References Cited

U.S. PATENT DOCUMENTS

| | | | |
|---|---|---|---|
| 3,918,815 A | | 11/1975 | Gadbois |
| 4,473,029 A | | 9/1984 | Fritz et al. |
| 4,546,060 A | | 10/1985 | Miskinis et al. |
| 4,553,033 A | | 11/1985 | Hubble, III et al. |
| 5,117,119 A | | 5/1992 | Schubert et al. |
| 5,148,217 A | | 9/1992 | Almeter et al. |
| 5,173,750 A | | 12/1992 | Laukaitis |
| 5,341,089 A | | 8/1994 | Heep |
| 5,471,282 A | * | 11/1995 | Hayashi et al. ............... 399/64 |
| 5,649,266 A | | 7/1997 | Rushing |
| 5,850,195 A | | 12/1998 | Berlien, Jr. et al. |
| 5,903,800 A | | 5/1999 | Stern et al. |
| 5,933,682 A | * | 8/1999 | Rushing ...................... 399/51 |
| 6,066,990 A | * | 5/2000 | Genest ......................... 331/25 |
| 6,100,767 A | * | 8/2000 | Sumi ............................ 331/11 |
| 6,111,442 A | * | 8/2000 | Aulet et al. .................. 327/156 |
| 6,144,024 A | * | 11/2000 | Rushing ............... 250/214 DC |
| 6,188,471 B1 | | 2/2001 | Jung et al. |
| 6,222,176 B1 | | 4/2001 | Rushing et al. |
| 6,225,618 B1 | | 5/2001 | Rushing et al. |
| 6,331,832 B1 | * | 12/2001 | Rushing ...................... 341/139 |
| 6,356,156 B2 | * | 3/2002 | Wesolowski .................. 331/10 |
| 6,370,408 B1 | * | 4/2002 | Merchant et al. ........... 600/322 |
| 6,396,355 B1 | * | 5/2002 | Rezin .......................... 331/18 |
| 6,427,057 B1 | * | 7/2002 | Hameister et al. ............ 399/74 |
| 6,505,010 B1 | * | 1/2003 | Izumizaki et al. ............ 399/39 |

OTHER PUBLICATIONS

U.S. patent application Ser. No. 09/873,465, Rushing, filed Jun. 4, 2001.
Scott Edwards, "Look Into 'The Eye from TI' For Precision Light Readings," Nuts & Volts Magazine, Nov., 1996, vol. 17 No. 11, T&L Publications, Inc. 430 Princeland Court, Corona, CA 92879, USA.
"TSL230 Evaluation Module, User's Guide," Texas Instruments, Inc. (nodate) L.
Paul Horowitz and Winfield Hill, "The Art of Electronics," Second Ed., 1989, Cambridge Univ. Press, 40 West 20th Street, New York, NY 10011 USA.

* cited by examiner

*Primary Examiner*—Michael Tokar
*Assistant Examiner*—Linh V Nguyen

(57) ABSTRACT

A densitometer using a light-to-frequency converter is disclosed. The converter outputs an oscillating signal with frequency characteristic of the incident light intensity. Digital controls may be input to the converter to set the frequency range of the output. The period count or frequency count of the converter output may be numerically divided to obtain a quotient within a small range. A lookup table is addressed according to the period count or frequency count, and return an offset scaled logarithm. The lookup table output is processed numerically to obtain a scaled density value. The converter may be adapted to process analog voltage inputs rather than light inputs. The logarithmic conversion then becomes applicable to a variety of fields besides densitometry.

40 Claims, 15 Drawing Sheets

| PERIOD COUNT "C" | DENSITY FOR S=10, N=100 "D" | LOOKUP TABLE INTEGER SCALED DENSITY | | |
|---|---|---|---|---|
| | | S=10, N=100 BINARY CODE=00 "H" | S=100, N=100 BINARY CODE=01 | S=100, N=10 BINARY CODE=10 |
| 40 | +LOG(C/40)=0 | D*300/3.00=0 | H+100=100 | H+200=200 |
| 41 | 0.011 | 01 | 101 | 201 |
| 42 | 0.021 | 02 | 102 | 202 |
| 43 | 0.031 | 03 | 103 | 203 |
| 44 | 0.041 | 04 | 104 | 204 |
| 45 | 0.051 | 05 | 105 | 205 |
| - | - | - | - | - |
| - | - | - | - | - |
| - | - | - | - | - |
| 394 | 0.993 | 99 | 199 | 299 |
| 395 | 0.995 | 99 | 199 | 299 |
| 396 | 0.996 | 100 | 200 | 300 |
| 397 | 0.997 | 100 | 200 | 300 |
| 398 | 0.998 | 100 | 200 | 300 |
| 399 | 0.999 | 100 | 200 | 300 |
| 400 | 1.000 | 100 | 200 | 300 |

FIG. 5

| PERIOD COUNT "C" | DENSITY FOR S=10, N=100 "D" | LOOKUP TABLE INTEGER SCALED DENSITY CORE VALUE S=10, N=100 |
|---|---|---|
| 40 | +LOG(C/40)=0 | D*297/3.00=0 |
| 41 | 0.011 | 01 |
| 42 | 0.021 | 02 |
| 43 | 0.031 | 03 |
| 44 | 0.041 | 04 |
| 45 | 0.051 | 05 |
| - | - | - |
| - | - | - |
| - | - | - |
| 394 | 0.993 | 98 |
| 395 | 0.995 | 98 |
| 396 | 0.996 | 99 |
| 397 | 0.997 | 99 |
| 398 | 0.998 | 99 |
| 399 | 0.999 | 99 |
| 400 | 1.000 | 99 |

FIG. 7

| PERIOD COUNT "C" | DENSITY FOR S=10, N=10 "F" | LOOKUP TABLE INTEGER SCALED DENSITY |
|---|---|---|
| 40 | LOG(C)-LOG(40)=0 | F*100=00 |
| 41 | 0.011 | 1 |
| 42 | 0.021 | 2 |
| 43 | 0.031 | 3 |
| 44 | 0.041 | 4 |
| 45 | 0.051 | 5 |
| - | - | - |
| - | - | - |
| - | - | - |
| 194 | 0.686 | 69 |
| 195 | 0.688 | 69 |
| 196 | 0.690 | 69 |
| 197 | 0.692 | 69 |
| 198 | 0.695 | 70 |
| 199 | 0.697 | 70 |
| 200 | 0.699 | 70 |

FIG. 11

| PERIOD COUNT "C" | LOOKUP TABLE INTEGER SCALED DENSITY, OFFSET & SCALED |
|---|---|
| 40 | 100*(LOG(C)-LOG(40))=0 |
| 41 | 1 |
| 42 | 2 |
| 43 | 3 |
| 44 | 4 |
| 45 | 5 |
| - | - |
| - | - |
| - | - |
| 285 | 85 |
| 286 | 85 |
| 287 | 86 |
| 288 | 86 |
| 289 | 86 |
| 290 | 86 |
| 291 | 86 |

FIG. 12

| PERIOD COUNT "C" | $V_{IN}$(VOLTS) N=1 (400/C)*.010=0.100 | LOG($V_{IN}$/10MV) N=1 -LOG(C/400)=1.00 | dB =20LOG($V_{IN}$/10MV) "E" | LOOKUP TABLE INTEGER SCALED LOGARITHM | | |
|---|---|---|---|---|---|---|
| | | | | N=1 BINARY CODE=00 "G" E*255/60=85 | N=10 BINARY CODE=01 G+85=170 | N=100 BINARY CODE=10 G+170=255 |
| 40 | | | 20.0 | 85 | 170 | 255 |
| 41 | 0.098 | 0.989 | 19.8 | 84 | 169 | 254 |
| 42 | 0.095 | 0.979 | 19.6 | 83 | 168 | 253 |
| 43 | 0.093 | 0.969 | 19.4 | 82 | 167 | 252 |
| 44 | 0.091 | 0.959 | 19.2 | 82 | 167 | 252 |
| 45 | 0.089 | 0.949 | 19.0 | 81 | 166 | 251 |
| . . . | . . . | . . . | . . . | . . . | . . . | . . . |
| 394 | 0.010 | 0.007 | 0.1 | 1 | 86 | 171 |
| 395 | 0.010 | 0.005 | 0.1 | 0 | 85 | 170 |
| 396 | 0.010 | 0.004 | 0.1 | 0 | 85 | 170 |
| 397 | 0.010 | 0.003 | 0.1 | 0 | 85 | 170 |
| 398 | 0.010 | 0.002 | 0.0 | 0 | 85 | 170 |
| 399 | 0.010 | 0.001 | 0.0 | 0 | 85 | 170 |
| 400 | 0.010 | 0.000 | 0.0 | 0 | 85 | 170 |

FIG. 14

DIGITAL DENSITOMETER USING LIGHT-TO-FREQUENCY CONVERTER

CROSS REFERENCE TO RELATED APPLICATIONS

This application is a Continuation-in-part of application Ser. No. 09/543,094, entitled DIGITAL DENSITOMETER USING LIGHT-TO-FREQUENCY CONVERTER, PERIOD COUNTER, AND LOOKUP TABLE, now abandoned, filed in my name on Apr. 3, 2000, and claims benefit of the filing date of that application, and is a CIP of Ser. No. 09/873,465 filed Jun. 4, 2001 U.S. Pat. No. 6,671,052.

Reference is made to co-pending U.S. patent application Ser. No. 09/873,465, entitled MULTI-CHANNEL DENSITOMETER, filed in my name on Jun. 4, 2001.

FIELD OF THE INVENTION

This invention relates generally to densitometers for measuring optical density. In particular, the invention relates to optical density measurement of ink-covered or toner-covered surfaces produced by apparatus such as printers, and to photographically printed areas.

BACKGROUND OF THE INVENTION

In electrostatographic apparatus such as copiers and printers, automatic adjustment of process control parameters is used to produce images having well regulated darkness or optical density. Copier and printer process control strategies typically involve measuring the transmissive or reflective optical density of a toner image on an exposed and developed area (called a "test patch") of an image receiver. Optical density has the advantage, compared to transmittance or reflectance measures, of matching more closely to human visual perception. A further advantage, especially for transmission density, is that density is approximately proportional to the thickness of the marking material layer, over a substantial range.

Typically, toned process control test patches are formed on the photoconductor in interframe regions of the photoconductor, i.e., between image frame areas. An "on-board" densitometer measures the test patch density, either on the photoconductor or after transfer of the patches to another support member. From these measurements, the machine microprocessor can determine adjustments to the known operating process control parameters such as primary charger setpoint, exposure setpoint, toner concentration, and development bias.

A transmission type of densitometer is particularly well suited to transmissive supports. In this type, a light source projects light, visible or infrared, through an object onto a photodetector such as a photodiode. In a copier/printer, the photoconductor passes between the light source and the photodetector. When the photoconductor has toner on the surface, the amount of light reaching the photodetector is decreased, causing the output of the densitometer to change. Based on this output, the amount of toner applied to the photoconductor can be varied as required in order to obtain consistent image quality. Another type of densitometer such as described in U.S. Pat. No. 4,553,033 to Hubble, III et al uses reflected light flux rather than transmitted light flux to determine density, and is particularly suited to opaque reflective supports.

One well-known approach to converting to a density measure uses an analog logarithmic amplifier, as suggested by the mathematical logarithm function in the definition of optical density:

$$D = -\log_{10}(T) \qquad \text{Equation (1)}$$

where D is optical density, and T is transmittance or reflectance (for transmission density or reflection density, respectively). The subscript "10" indicates that the logarithm is to the base 10. Since T must be between 0 and 1, the logarithm of T is negative, and the minus sign (−) in equation (1) provides positive values for density, D.

The following U.S. Patents, for example, all teach the use of an analog logarithmic amplifier in a densitometer: U.S. Pat. No. 3,918,815 to Gadbois, U.S. Pat. No. 5,148,217 to Almeter et al, U.S. Pat. No. 5,173,750 to Laukaitis, and U.S. Pat. No. 5,903,800 to Stern et al. The high cost of precision analog logarithmic amplifiers does not seriously deter their use in expensive laboratory instruments. However, the high cost of analog logarithmic amplifiers has been an obstacle to the wide use of densitometers as built-in components within moderately priced copiers, printers, and other products.

Digital approaches to densitometer design have been developed, as digital electronics improve in performance and decline in price, relative to analog logarithmic amplifiers. One digital approach in the prior art is to obtain a photodetector voltage signal representing intensity of transmitted or reflected light and convert this analog signal to digital form. The digital value is then used to enter a stored lookup table (LUT) of and density values. The digital density value corresponding to the digital intensity value is read from the LUT. To cover a reasonably large range of density with the required resolution, an amplifier with selectable gain has been used.

U.S. Pat. No. 5,117,119 to Schubert et al discloses an automatic gain selection, i.e., an "auto-ranging" electronic circuit, along with a second LUT, to obtain high accuracy and resolution over an increased range of large densities. The first (or "base") LUT contains density values corresponding to an analog-to-digital (A/D) converter output for the lowest gain. The second (or "range") LUT is much smaller than the first LUT and contains the relative density corresponding to each available gain. It provides the density increment associated with the gain selected. The two LUT outputs are summed to obtain the actual density measurement. LUT approaches are also disclosed by Rushing et al in U.S. Pat. Nos. 6,222,176 and 6,225,618, and by Rushing in U.S. Pat. No. 6,331,832.

Prior art digital densitometers, such as those in the aforementioned disclosures, typically have an analog amplifier stage near the photodetector end of the circuit, before converting the measurement signal to digital form. While the signal is in analog form, it is especially vulnerable to corruption by electrical noise and small voltage offsets.

Moreover, the analog amplifiers in prior art densitometers have a selectable gain, requiring the switching of the analog measurement signal. Even small noise levels and error introduced in switching can have a relatively large effect on a small measurement signal. For example, integrated circuit analog switches typically have an "ON" resistance of several 10's to a few 100's of ohms, which varies with the voltage being switched and other factors. This resistance alters the amplifier gain, introducing a variable error, which is difficult to compensate. Unwanted switching transients during gain changes compound the problem.

Another digital approach to digital densitometry is suggested, without design specifics, by Edwards in the November, 1996 issue of "Nuts and Volts" magazine. Edwards suggests using a light-to-frequency (L-to-F) converter integrated circuit as a photodetector in a densitometer. In U.S. Pat. No. 6,188,471, Jung et al disclose the use of such L-to-F converters for the measurement of optical properties such as color, gloss, and translucence. Jung et al do not address the logarithmic conversion underlying optical density measurement.

In a L-to-F converter, the output frequency is proportional to the incident light intensity. Reflected or transmitted light incident on the converter can be measured in intensity by one of two methods, as suggested in the "TSL230 Evaluation Module Users Guide," by Texas Instruments, Inc. One method is to count the converter output pulses during a fixed time period, yielding a frequency count Optical density can then be determined from the known relationship of intensity, frequency and optical density. The other method is to measure the period or pulse width by counting clock pulses during a single output pulse from the converter, yielding a period count. Optical density can then be determined from the known relationship of intensity, converter output period and optical density.

In the frequency count method, updated density measurements are obtained only as often as the fixed counting time period. This counting time must be long enough to provide a large frequency count to obtain good density resolution, even for low frequencies (high optical density).

In the period count method, updated density measurements are obtained with every measured period For very high incident light intensities (low optical density) the frequency is very high, and the period so short that the count of clock pulses is small, and the conversion to density has insufficient resolution. For very low incident light intensities (high optical density), the frequency is very low, and the period so long that the count of clock pulses may cover a very large range. Such a large range is unwieldy, and if used to address a LUT, the LUT must be very large.

For frequency measurement over a wide range, the frequency count and period count methods have been combined, with automatic switching between the two, to get optimum resolution for any input frequency. This approach is described by Horowitz and Hill in "The Art or Electronics," as having been used commercially in the Hewlett Packard Co. model 5315A.

U.S. Pat. No. 6,144,024, to Rushing, combines the frequency count method and the period count method, to achieve wider density measurement range. Dual counters and dual density LUTs are used For very high densities (low light intensity at the sensor, and low L-to-F output frequency), the large period counts require a large LUT, i.e., a LUT with many entries.

Since logarithmic conversion is at the heart of densitometry, logarithmic converters in other contexts may bear on densitometer applications. U.S. Pat. No. 5,341,089 to Heep discloses a digital circuit to convert an analog voltage input to decibel (dB) units. The dB output is defined as 10 times the logarithm (base 10) of the ratio of the power of the input signal relative to a reference power level. This logarithmic conversion is of the same general type as used within densitometers, according to equation (1). The Heep disclosure has no selectable gain and no auto-ranging. Large inputs must first be scaled down by a manually adjusted voltage divider to obtain an input within the operating range, and an output from a second LUT is added to compensate for the scaling down. Interpolation between LUT values is applied to obtain the desired accuracy, adding complexity to the circuit and lengthening the time required obtaining a measurement update.

SUMMARY OF THE INVENTION

One object of the present digital densitometer invention is to obtain a reasonably rapid update rate and good density resolution over a wide density range, with minimum circuit complexity. The present densitometer invention uses only a single lookup table, which can be relatively small, and is less complex than digital densitometer circuits in the prior art.

Another object of the present invention is to process the measurement signals more completely in digital form, to obtain the superior noise immunity of digital signal processing. The analog light intensity signal is immediately converted to a digital form, i.e., a variable-frequency square wave oscillating between logic "0" and logic "1", within the light-to-frequency converter portion of the circuit. In subsequent stages, the circuit processes the signal digitally. No switching of analog signals is involved.

It is still another object of the present invention to provide a digital logarithmic converter circuit, applicable not only within densitometers, but also in other applications where there is need to convert an input to an output proportional to the logarithm of the input. A digital logarithmic converter could be applied in a variety of fields. In photography the "f-stop" measure is proportional to the logarithm of aperture area In chemistry the "pH" acid-base measure is proportional to the logarithm of ion concentration. In acoustics, the "dB" sound intensity measure is proportional to the logarithm of the sound power. In electronic circuits, "dB gain" is proportional to the logarithm of the voltage gain. In general, any signal varying over a wide dynamic range may be evaluated more readily without switching gain or scale by first passing the signal through a logarithmic converter.

To obtain the aforesaid objects, a densitometer using a light-to-frequency (L-to-F) converter is disclosed. Transmitted or reflected light is converted to an oscillating signal with frequency characteristic of the light intensity incident on the converter. With a programmable L-to-F converter, digital controls for sensitivity and/or divide-by ratio are input to the L-to-F converter to obtain an output frequency within a relatively narrow range. A period counter measures the period of the converter output. A LUT address is formed at least partially from the period count. The LUT output is proportional to the logarithm of the period count, with a positive or negative offset. The LUT output offset may be removed by shifting the output value according to the programmed sensitivity and divide-by ratio, to obtain a scaled density value, or at least the low-order digits of a scaled density value.

With a non-programmable L-to-F converter, large period counts may be numerically divided such that the quotient, i.e., the divided period count, is within a relatively narrow range. A LUT is addressed according to the period count, or divided period count. The number of entries, i.e., number of addresses, in the LUT is small, owing to the period count, or divided period count, being within a relatively narrow range. The LUT output is proportional to the logarithm of the period count, or divided period count, with a positive or negative offset. The LUT output offset may be shifted by addition or subtraction, and thereby removed, according to the divisor used to obtain the divided period count, to obtain a scaled density value.

To extend the measurement range to higher light intensities incident on the L-to-F converter (for lower density test samples), a frequency count is used to address the same LUT addressed by the period count when measuring higher densities. One aspect of the invention uses a relatively high intensity light emitter, and switches automatically to the frequency count addressing when the period count is too small for acceptable density resolution. The LUT output is processed according to whether the LUT address was derived from period count or frequency count, and according to the divisor used. Only a single LUT, relatively small in size, is addressed according to either period count or frequency count, enabling a large density measurement range.

The L-to-F converter may be adapted to process analog voltage inputs rather than light inputs. The logarithmic conversion then becomes applicable to a variety of fields besides densitometry.

The invention and its various advantages will become more apparent to those skilled in the art from the ensuing detailed description of the preferred embodiments, reference being made to the accompanying drawings.

BRIEF DESCRIPTION OF THE DRAWINGS

The subsequent description of the preferred embodiments of the present invention refers to the attached drawings wherein:

FIG. 5 is a table showing how the scaled density values are determined for pre-loading into the LUT of the first preferred embodiment;

FIG. 7 is a table showing how the scaled density values are determined for pre-loading into the LUT of the second preferred embodiment;

FIG. 11 is a table showing how the scaled density values are determined for pre-loading into the LUT of the third preferred embodiment;

FIG. 12 is a table showing how the scaled density values are determined for pre-loading into the LUT of the fourth preferred embodiment;

FIG. 14 is a table showing how, for one example, the scaled logarithm values are determined for pre-loading into the LUT of a general logarithmic converter circuit.

DETAILED DESCRIPTION OF THE PREFERRED EMBODIMENTS

I. Electrophotographic Printing Machine Environment

Because apparatus of the general type described herein are well known, the present description will be directed in particular to elements forming part of, or cooperating more directly with, the present invention. While the invention will be described with reference to imaging apparatus and particularly to an electrophotographic system, the invention can also be used in other imaging apparatus and in applications not in the imaging field.

Figure 1:
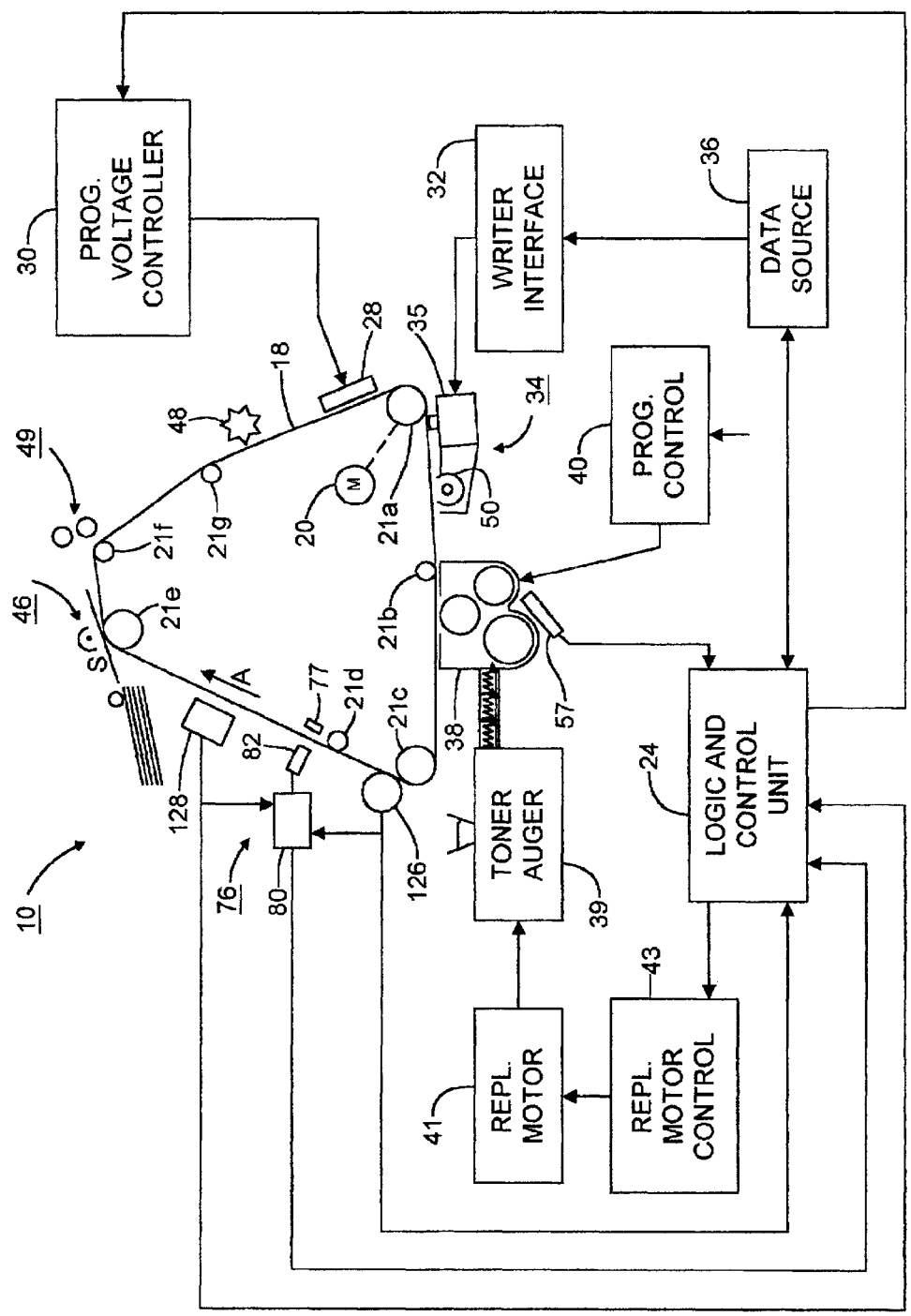
FIG. 1 is a side elevational view in schematic form of an electrophotographic apparatus to illustrate one environment for the use of this invention.

With reference to the electrophotographic copier and/or printer machine 10 as shown in FIG. 1, a moving recording member such as photoconductive belt 18 is entrained about a plurality of rollers or other supports 21a–21g one or more of which are driven by a motor so as to advance the belt in a direction indicated by an arrow "A" past a series of workstations of machine 10. A logic and control unit 24, which has a digital computer, has a stored program for sequentially actuating the workstations in response to signals from various sensors and encoders, as is well known.

A primary charging station 28 sensitizes belt 18 by applying a uniform electrostatic charge of predetermined primary voltage $V_0$ to the surface of the belt. The output of the charging station is regulated by a programmable voltage controller 30, which is in turn controlled by logic and control unit 24 to adjust primary voltage $V_0$ for example through control of electrical potential ($V_{grid}$) to a grid that controls movement of corona charges from charging wires to the surface of the recording member, as is well known. Other known forms of chargers, including roller chargers, may also be used.

At an exposure station 34, projected light from a write head 35 dissipates the electrostatic charge on the photoconductive belt to form a latent image of a document to be copied or printed. The write head preferably has an array of light-emitting diodes or other light source such as a laser or other spatial light modulator for exposing the photoconductive belt picture element (pixel) by picture element with a regulated intensity and exposure, $E_0$. Alternatively, the exposure may be by optical projection of an image of a document or a patch onto the photoconductor.

Where a light-emitting diode or other electro-optical exposure source or writer is used, image data for recording is provided by a data source 36 for generating electrical image signals. The data source 36 may be a computer, a document scanner, a memory, a data network, etc. Signals from the data source and/or logic and control unit may also provide control signals to a writer interface 32 for identifying exposure correction parameters in, for example, a LUT for use in controlling image density. Travel of belt 18 brings the areas bearing the latent charge images into a development station 38. The development station has one (more if color) magnetic brush in juxtaposition to, but spaced from, the travel path of the belt Magnetic brush development stations are well known. For example, see U.S. Pat. No. 4,473,029 to Fritz et al and U.S. Pat. No. 4,546,060 to Miskinis et al. Other types of development stations may be used as is well known and plural development stations may be provided for developing images in plural colors or with toners of different physical characteristics.

Logic and control unit 24 selectively activates the development station in relation to the passage of the image areas containing latent images to selectively bring the magnetic brush into engagement with or a small spacing from the belt. The charged toner particles of the engaged magnetic brush are attracted imagewise to the latent image pattern to develop the pattern.

Conductive portions of the development station, such as conductive applicator cylinders, act as electrodes. The electrodes are connected to a variable supply of D.C. potential $V_B$ regulated by a programmable controller 40. Details regarding the development station are provided as an example, but are not essential to the invention.

A transfer station 46 as is also well known is provided for moving a receiver sheet "S" into engagement with the photoconductive belt in register with the image for transferring the image to a receiver. Alternatively, an intermediate member may have the image transferred to it and the image may then be transferred to the receiver. A cleaning station 48 is also provided subsequent to the transfer station for removing toner from the belt 18 to allow reuse of the surface for forming additional images. In lieu of a belt, a drum photoconductor or other structure for supporting an image may be used. After transfer of the unfixed toner images to a receiver sheet, such sheet is detacked from the belt and transported to a fuser station 49 where the image is fixed.

The logic and control unit provides overall control of the apparatus and its various subsystems as is well known. Programming commercially available microprocessors is a conventional skill well understood in the art.

Figure 2:
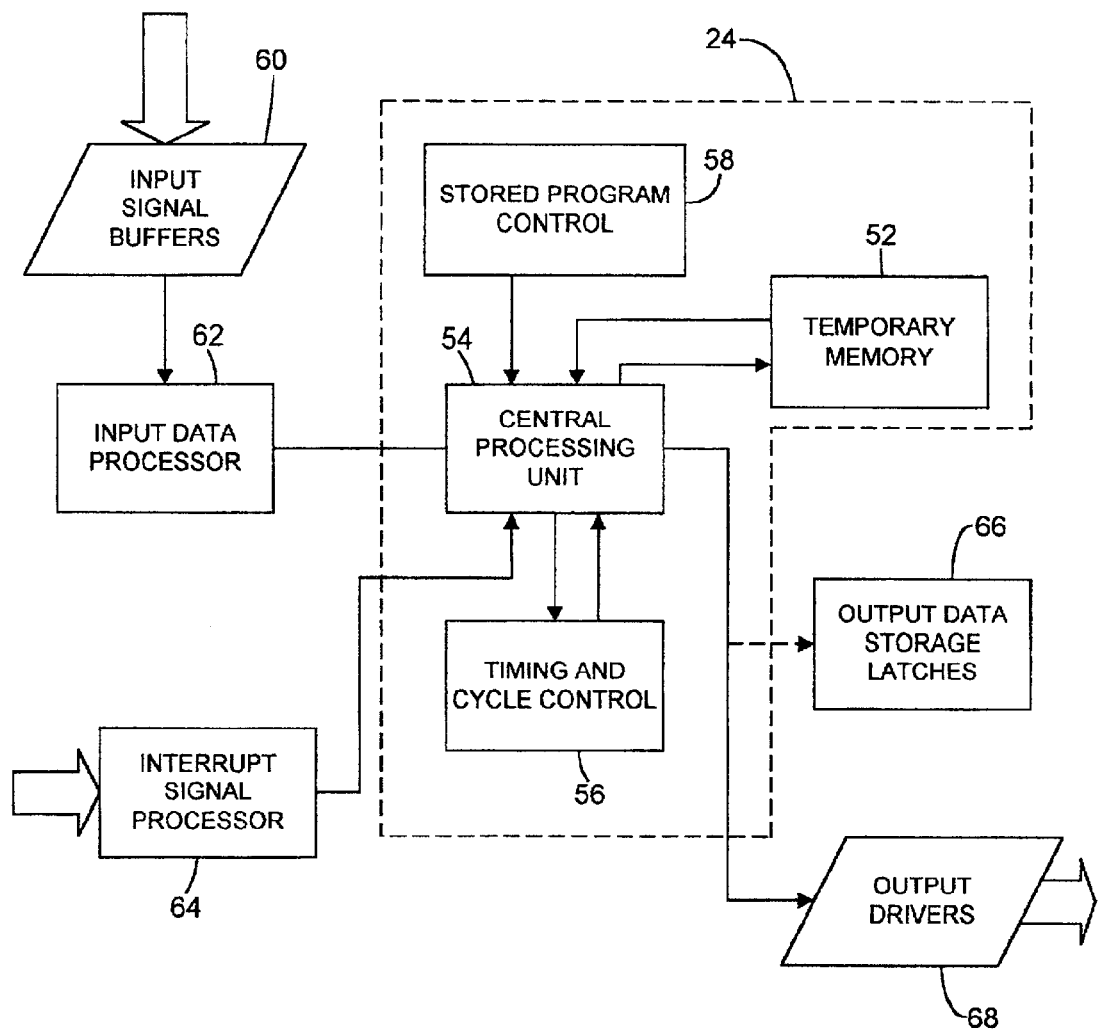
FIG. 2 is a block diagram of a logic and control unit for controlling the apparatus of FIG. 1.

Referring to FIG. 2, a block diagram of a typical logic and control unit 24 is shown. The logic and control unit comprises temporary data storage memory 52, central processing unit 54, timing and cycle control unit 56, and stored program control 58. Data input and output is performed sequentially through or under program control. Input data are applied either through input signal buffers 60 to an input data processor 62 or through an interrupt signal processor 64. The input signals are derived from various switches, sensors, and the A/D converters that are part of the apparatus 10 or received from sources external to machine 10.

The output data and control signals are applied directly or through storage latches 66 to suitable output drivers 68. The output drivers are connected to appropriate subsystems. Process control strategies generally utilize sensors to provide real-time control of the electrostatographic process and to provide "constant" image quality output from the user's perspective.

Referring again to FIG. 1, one such sensor for process control may be a densitometer 76 to monitor development of test patches in non-image areas of photoconductive belt 18, as is well known in the art. See for example U.S. Pat. No. 5,649,266 to Rushing. The densitometer measurements are needed to insure that the transmission or reflection density of toned areas on the belt is maintained. The densitometer may include a visible or infrared light-emitting diode (LED) 77 that shines light through the belt or reflected by the belt onto a light detector 82, which is connected to a densitometer circuit 80. The photodiode detector may be separate from the densitometer circuit, as shown in FIG. 1, or may be on the same circuit board as the densitometer circuit components.

For a transmission densitometer, emitter 77 may be on the untoned side of belt 18 and detector 82 on the toned side, as shown. Alternatively, the reverse arrangement is also workable. For a reflection densitometer, the emitter and detector would both be on the toned side of the belt. The detector generates an electrical signal that varies directly with the flux of light received. The densitometer circuit converts the detector signal to a density value.

A rotary encoder 126 engaging belt 18 outputs logic pulses corresponding to the motion of the belt. The pulse output enables the densitometer 76 to collect density readings synchronously with the belt motion. The pulse output is also connected to LCU 24 for the purpose of synchronizing the operation of the various workstations. A "sync" pulse motion sensor 128 outputs a "sync" pulse, preferably only one for each belt once-around, to provide an indication of the absolute position of belt 18.

In the case of transmission density, the total, or gross, measured density value is reduced by the density value of a bare untoned patch, to obtain a value $D_{OUT}$, representative of the net toner density. The net density signal is also representative of the thickness of the toner deposit averaged over the measurement area, and also representative of the toner mass per unit area. The $D_{OUT}$ signal may be used to adjust process parameters $V_0$, $E_0$, or $V_B$. The $D_{OUT}$ signal may also be used to assist in the maintenance of the proper concentration of toner particles in the developer mixture by having the logic and control unit provide control signals to a replenisher motor control 43.

Replenisher motor control 43 controls replenisher motor 41 that in turn drives a toner auger 39 for feeding new toner particles into development station 38. A toner concentration monitor probe 57 provides signals to the logic and control unit about relative concentration of toner particles to carrier particles in the developer mix Another sensor useful for monitoring process parameters is an electrometer probe 50, mounted at a location preferably downstream of corona charging station 28, relative to the direction of the movement of belt 18. In FIG. 1 electrometer probe 50 is mounted immediately downstream of writehead 35.

II. First Preferred Densitometer Embodiment (Programmable L-to-F Converter, LUT Containing Complete Density Values)

Figure 3:
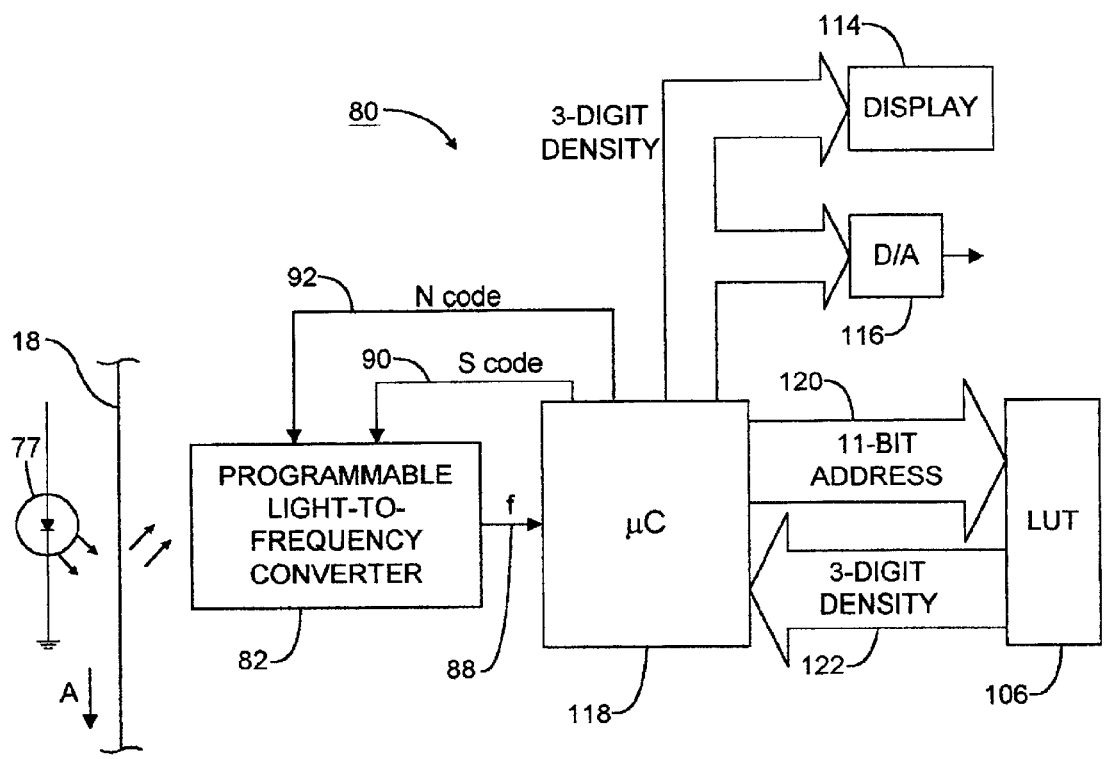
FIG. 3 is a block diagram of a densitometer according to the first preferred embodiment of the present invention.

Referring to FIG. 3, densitometer circuit 80 according to the first preferred embodiment includes a programmable L-to-F converter 82. Light from LED 77, transmitted through belt 18 moving in direction "A" impinges on programmable L-to-F converter 82. Within programmable L-to-F converter 82, a light sensor includes an area array of 100 substantially identical photodiodes, all on a single integrated circuit chip. Such a chip is commercially available as model TSL230, developed by Texas Instruments, Inc., and now available from Texas Advanced Optoelectronic Solutions (TAOS), Inc. Berlien, Jr. et al in U.S. Pat. No. 5,850,195 disclose technology detail beyond the level of the device data sheet and the User's Guide. The TSL230 chip features external addressability of defined subsets of the array, along with capability to sum the photocurrents from the selected subset of photodiodes. Each defined subset has a different number of photodiodes (1, 10, and 100), providing a real-time programmable light sensitivity, S, with programmable relative values of 1, 10, or 100.

Within the same chip the photocurrent sum is converted to a high-level periodic signal 88 whose frequency,f, is proportional to the light intensity and the photocurrent sum. Also included within the TSL230 is a real-time programmable divide-by-N (N=1, 2, 10, or 100) frequency divider. The TSL230 conveniently integrates the aforementioned functions on a single chip, but it is understood that other embodiments could have the individual functions accomplished with separate components.

Equation (1) defines optical density as the negative logarithm of transmittance or reflectance. Light incident on the TSL230 produces an output frequency proportional to light intensity, or an output period inversely proportional to light intensity. Therefore a densitometer using the TSL230 to detect transmitted or reflected light characterizes density by the negative logarithm of the TSL230 frequency, or the positive logarithm of the TSL230 period, with a numerical offset corresponding to the proportionality constant. This preferred embodiment is based on a measurement of the TSL230 output period.

With continuing reference to FIG. 3, the variable-frequency square wave output from L-to-F converter 82 is input to a period counter, within a microcontroller (µC) 118. An example of such a microcontroller is the Microchip Corporation model PIC16C621. The period counter outputs a "period count", i.e., a count of high-frequency clock pulses during a single cycle or halfcyle of the square wave. The period count is thus proportional to the period of a single cycle of the square wave. Converter parameter logic within microcontroller 118 compares the period count to upper and lower limits. If the period count is outside the limits, microcontroller 118 changes at least one of the two L-to-F programming parameters S and N. Microcontroller 118 does this by changing the S code 90 or N code 92 output to programmable L-to-F converter 82.

Figure 4:
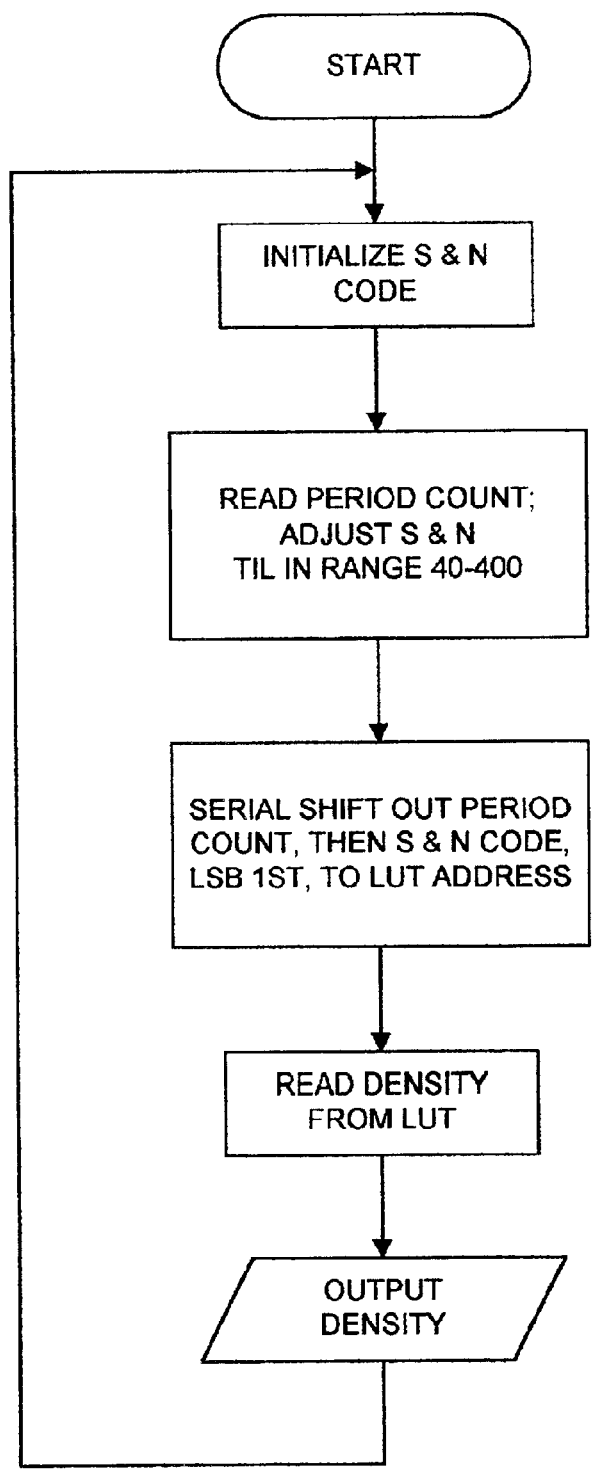
FIG. 4 is a program flowchart for the microcontroller of the first preferred embodiment of the present invention.

Preferably, the counter and converter parameter logic functions are programmed within microcontroller 118. Alternatively, the counter and converter parameter logic functions may be accomplished with discrete non-programmable or "hard-wired" digital circuitry. The microcontroller of this preferred embodiment is programmed according to the flowchart of FIG. 4.

In this first preferred embodiment, the TSL230 parameters S and N are changed as required to yield a period count in the range of 40 to 400. The 400:40 ratio is equivalent to a 10:1 ratio, the same as the ratio of S values (100:10:1) and N values (100:10) used in the TSL230. This 10:1 ratio corresponds to a density increment of 1.0 density units. Thus a given selection of S and N values accommodates a density range of 1.0, and switching to the next larger or smaller value of S or N extends the density range by 1.0 density units. With the S and/or N values set automatically according to the density of the test sample being measured, the densitometer is described as "auto-ranging."

Referring again to FIG. 3, the 9-bit period count (40 to 400 decimal) is combined with a 2-bit binary code for the 1-of-3 selection of the S and N parameters to form a complete 11-bit address 120, input to a LUT 106. LUT 106 may be a separate integrated circuit component, such as a programmable read-only memory (PROM). Alternatively, if sufficient memory is available, LUT 106 may be contained within microcontroller 118.

Preferably, for an orderly LUT organization, the parameter code forms the 2 higher-order address bits, and the period count forms the remaining 9 lower-order bits, with the least-significant bit (LSB) of the count connected to the LSB of the address, and so forth. LUT 106 is pre-loaded with the scaled density values corresponding to the period count and the S and N parameter values. When microcontroller 118 reads a particular LUT entry, a scaled density value 122 with 3 decimal digits is returned to the microcontroller. The zero density reference point in LUT 106 corresponds to the light intensity at the sensor presumed to come from a zero-density sample (ideally 100% transmissive or 100% reflective). If, owing to a dim light emitter, for example, the zero-density sample actually yields a non-zero output from LUT 106, this value may be stored as a reference value in microcontroller 118, and subtracted from subsequent raw density readings to obtain corrected readings. In an alternative "zeroing" procedure, the light emitter is adjusted such that a raw measurement value of zero is in fact obtained for the zero-density sample.

Depending on the application, microcontroller 118 may output the scaled density value to one or more output devices. Examples of such output devices include (a) a decimal display device, (b) a hexadecimal display device, (c) a binary display device, (d) a graphic display device, (e) a digital data storage device, (f) a digital connection to a host computer device or network, (g) a digital-to-analog (D/A) converter, and (h) an actuator for adjusting subsequent sample processing. For the present embodiment, FIG. 3 shows the 3-digit scaled density value connected to a display device 114 and a D/A converter 116.

The table of FIG. 5 shows how the scaled density values are determined, using a scale factor of 100, for pre-loading into LUT 106. Values from columns designated "C", "D", and "H" are used in computing values in columns following to the right, according to the equations at the top of each column. Every integer from 0 to 300 is contained in at least one LUT entry, giving true resolution of 0.01 density units. The total density range is 0 to 3.00, requiring 3 different combinations of S and N values.

When a particular LUT address is read, LUT 106 outputs the complete scaled density value that was pre-loaded, preferably with no further processing required. However, in some cases the locations of LUT 106 may be too small to contain all the digits of the scaled density value. For example, 8-bit entries in LUT 106 could not contain complete 9-bit scaled density values. In such a case the low-order bits, as many as fit, are pre-loaded into LUT 106, while the high-order bit(s) are set "on-the-fly", i.e., in real-time, according to the parameter code and the period count. Preferably, microcontroller 118 performs the functions of setting the parameter code for S and N, forming the LUT address from the period count and parameter code, reading the LUT, if necessary appending the high-order scaled density digit(s), and outputting the complete scaled density value.

III. Second Preferred Densitometer Embodiment (Programmable L-to-F Converter, LUT Containing Only Low-Order Density Digits)

Figure 6:
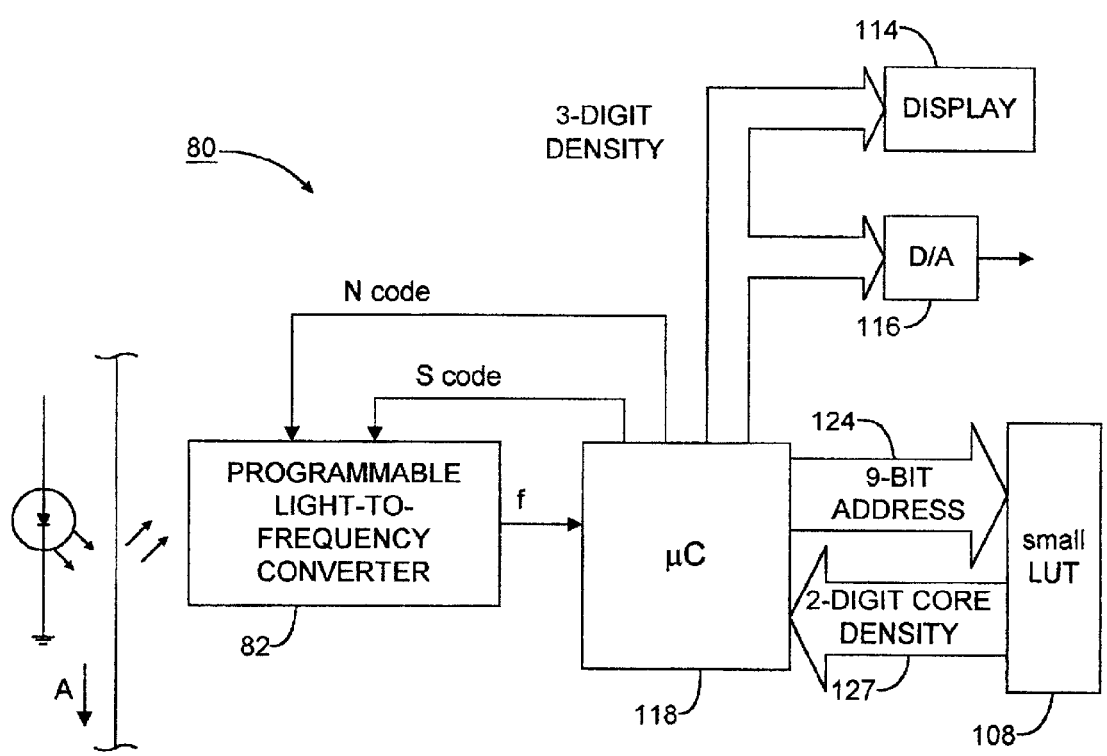
FIG. 6 is a block diagram of a densitometer according to the second preferred embodiment of the present invention.

Referring to FIG. 6, densitometer circuit 80 according to the second preferred embodiment includes programmable L-to-F converter 82 as in the first preferred embodiment. Within microcontroller 118 a period counter functions as in the first preferred embodiment. The sensitivity S, and divide-by ratio, N, are programmed as in the first preferred embodiment.

Unlike the first preferred embodiment, a smaller LUT 108 is used, with only a 9-bit address 124. The 9-bit period count forms the complete LUT address, rather than only the low-order address bits. Small LUT 108 is pre-loaded with the 2 low-order or "core" decimal digits of the scaled density values, according to the period count. When microcontroller 118 reads a particular LUT entry at a specific address, small LUT 108 returns a 2-digit core scaled density value 127.

Density scaling for an embodiment of this type begins with a choice of a base-B number system (e.g., base-2 or base-10), in which to represent the scaled density values. The core density range to be pre-loaded into small LUT 108 is scaled to K digits covering a range of 0 to $B^K-1$. Small LUT 108 is pre-loaded with these K digits in base-B. These values may be pre-loaded into small LUT 108 using any code, such as binary, binary-coded decimal, or ASCII, that can be interpreted when LUT 108 is read. When small LUT 108 is read, it outputs the K-digit base-B scaled density value, representing the low-order or core digits. The remaining higher-order digits of the scaled density value are set according to the parameter code.

Depending on the application, the density measurement result may be output to one or more output or display devices, or to a host computer device or network. As shown in FIG. 6, the 3-digit scaled density output is serially output to numeric display device 114 and D/A converter 116.

To scale the density values in this embodiment, a decimal representation (B=10) is chosen. The LUT is loaded with 2-digit, 0 to $10^2-1=99$ scaled density values. The table in FIG. 7 shows how the scaled density values to be pre-loaded into the LUT are determined for each period count. An advantage over the first preferred embodiment is that the LUT of FIG. 6 has only ⅓ as many entries, while the total range and resolution are about the same for both embodiments. The remaining $3^{rd}$ (highest-order) digit (0, 1, or 2) is set according to the parameter code, to complete the 3 digit scaled density value. The total range of the scaled density values is 0 to 299. Every integer value from 0 to 99 is contained in at least one LUT entry, so there are no skipped values, giving a true resolution of 0.01 density units.

Figure 8:
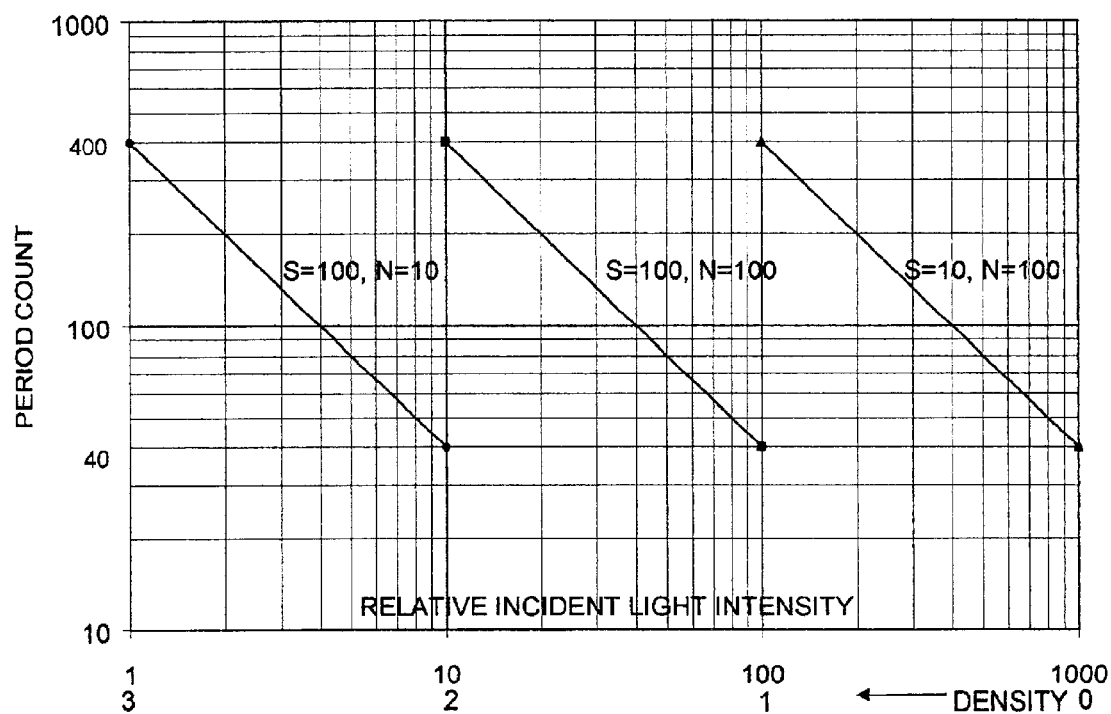
FIG. 8 is a graph of the programmable light-to-frequency converter performance characteristic, on logarithmic scales, relating the period count to the incident light intensity and density, applicable to the first and second preferred densitometer embodiments.

Referring to FIG. 8, the graph shows the period count versus incident light intensity on a log-log scale, applicable to both the first and second preferred densitometer embodiments. The straight line segments correspond to fixed values for sensitivity S and frequency divide-by ratio N, wherein the period count is inversely proportional to light intensity. Each discontinuity corresponds to a switch in S or N value. In each segment the period count ranges from 40 to 400, and the intensity changes by a factor of 10. This corresponds to a density increment of 1.0 density units.

For an alternative scaling for this same embodiment, a binary representation (B=2) for scaled density values may be used. For this alternative, the LUT is loaded with 7-bit scaled density values in the range of 0 to $2^7-1=127$. The higher-order 2 bits are set by the binary parameter code (00, 01, or 10), to complete the 9-bit scaled density value. Over the 3 decades of light intensity, the total range of the scaled density values is 0 to 383, representing a range of 0 to 3.00 density units. All 9 binary digits are output to a display or other output device.

IV. Third Preferred Densitometer Embodiment (Programmable L-to-F Converter, LUT Containing Offset Density Values)

Figure 9:
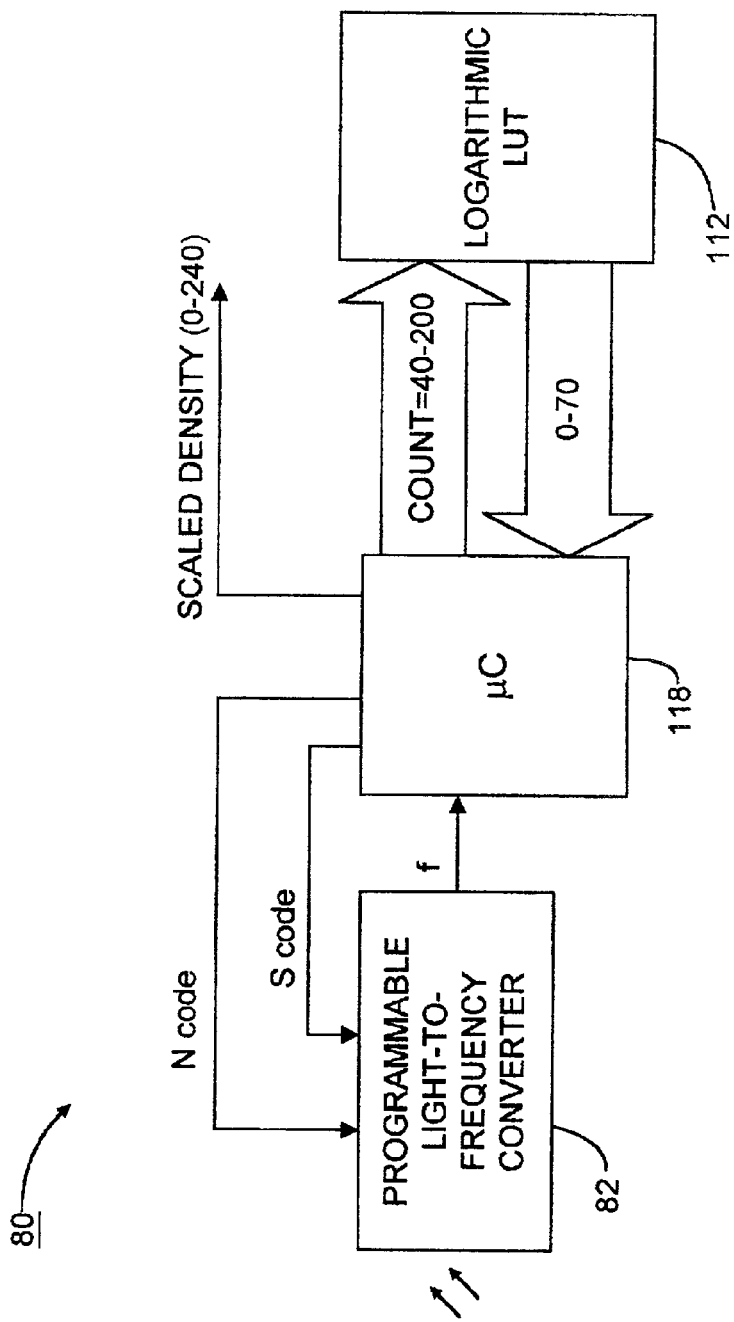
FIG. 9 is a block diagram of a densitometer according to the third preferred embodiment of the present invention.

Referring to FIG. 9, densitometer circuit 80 includes programmable L-to-F converter 82, as in the first and second preferred embodiments. Within microcontroller 118 a period counter functions as in the first and second preferred embodiments, to measure the period of the output of programmable L-to-F converter 82. The sensitivity S, and divide-by ratio N, are changed in real-time, according to sample density and the light intensity incident on programmable L-to-F converter 82, to obtain a period count in the range of 40 to 200. The minimum count of 40 permits output resolution of 0.01 density units. The maximum count of 200 permits a more rapid measurement update rate, compared to the first and second preferred embodiments, which allow period counts up to 400.

Figure 10:
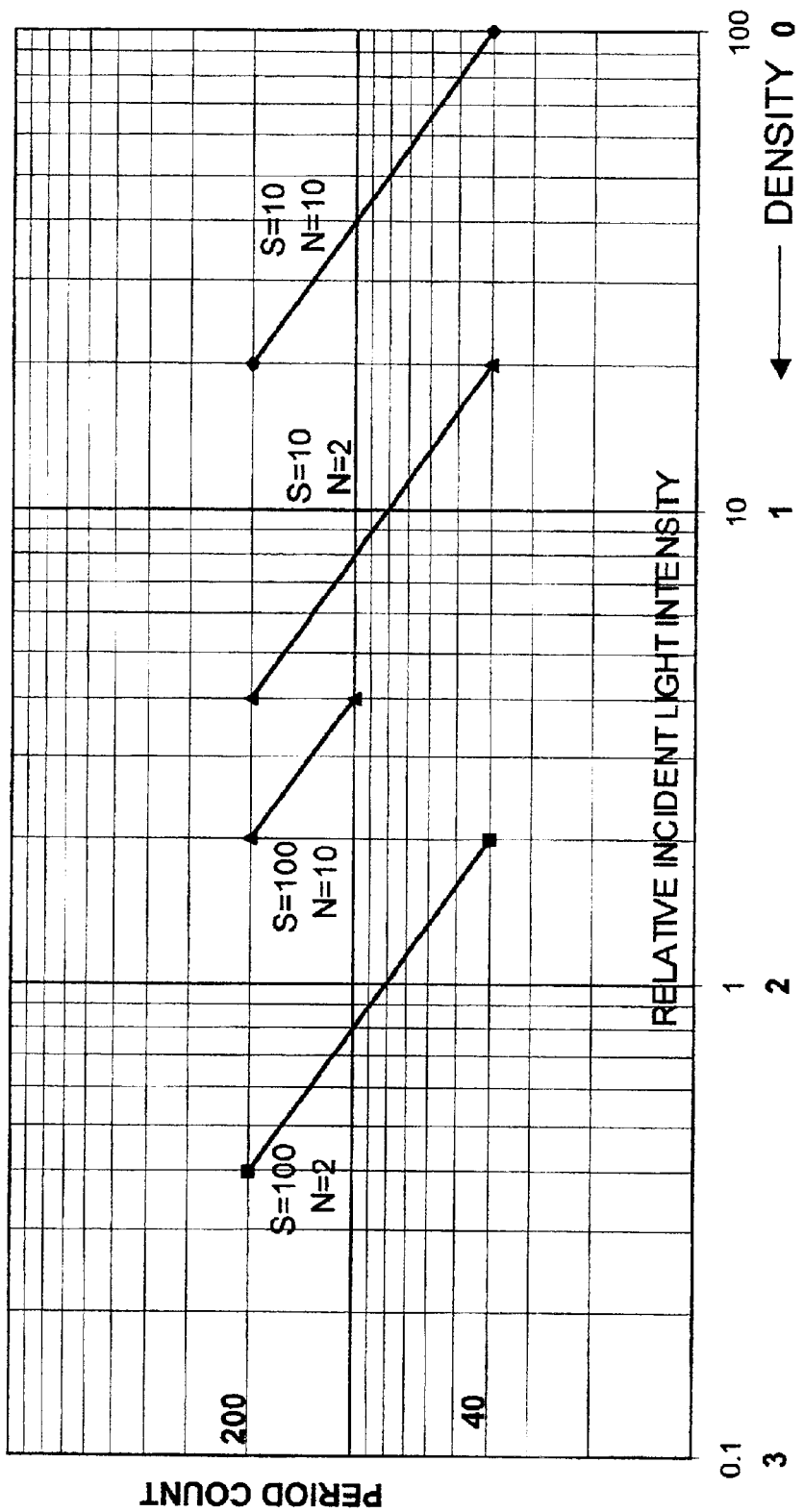
FIG. 10 is a graph of the programmable light-to-frequency converter performance characteristic, on logarithmic scales, relating the period count to the incident light intensity and density, applicable to the third preferred densitometer embodiment.

FIG. 10 shows a graph of the period count versus incident light intensity on a log-log scale. Relative optical density is also shown on the horizontal scale, increasing from right to left. As shown in FIG. 10, the density measurement range is 0 to 2.4, using four combinations of the S and N programmed values. A given period count corresponds to a specific density value, according to the S and N values. The right-most graph segment, with S=10 and N=10 and density values from 0 to 0.7, may be considered a reference segment. Density values for the other segments are offset from the reference segment by 0.7, 1.0, or 1.7 density units, for (S,N) values of (10,2), (100,10), and (100,2) respectively.

Referring again to FIG. 9, a small (161 entries for period counts from 40 to 200) logarithmic LUT 112 is addressed according to the period count. The actual numerical LUT address values need not be identical to the period counts; there need only be a defined correspondence between period count and LUT address. LUT 112 is pre-loaded with logarithm values of the respective period counts, offset and scaled as shown in the table of FIG. 11. The LUT entries match the density values of the reference segment of the graph in FIG. 10, scaled by a factor of 100. Microcontroller 118 adds to the LUT output, according to the current S and N values, to obtain the scaled density value. Values of 70, 100, or 170 are added for (S,N) values of (10,2), (100,10), and (100,2) respectively, to provide a range of scaled density values from 0 to 240.

V. Fourth Preferred Densitometer Embodiment (Non-Programmable L-to-F Converter, Divided Period Count)

A non-programmable L-to-F converter designated TSL235, available from TAOS, Inc., is used in this preferred embodiment. The TSL235 is smaller, less costly, and has only 3 leads, compared to the 8-lead TSL230. The output frequency is proportional to incident light intensity, with a fixed high-sensitivity and non-programmable proportionality constant.

A period count is obtained as in the first three preferred embodiments. A period count ranging from 40 to 4000 covers a density range of 0 to 2.0 with resolution of 0.01 density units. Without capability of programming the TSL235 for reduced sensitivity, a relatively dim light emitter is used so that the period count is at least 40, even for low-density samples. In the microcontroller of this embodiment, period counts exceeding 1164 are divided by 16, and period counts between 292 and 1164, inclusive, are divided by 4. The quotients are rounded to the nearest integer, obtaining divided period counts within the LUT count range of 40 to 291.

The resultant counts, within the range of 40 to 291, are used to address a fairly small LUT of 252 entries, containing logarithm values of the counts, offset and scaled. The offset and scaling are such that the LUT entries scale density by a factor of 100, as shown in the table of FIG. 12. Every integer value from 0 through 86 is contained in at least one LUT entry, with no skipped values, providing resolution of 0.01 density units. In the microcontroller, subsequent numerical processing adds the offset associated with division by 4 (offset of 0.60 density units) or division by 16 (offset of 1.20 density units), to obtain scaled density values over the entire range, up to 0.86+1.20=2.06 density units, for period counts of about 4656.

VI. Fifth Preferred Densitometer Embodiment (Non-Programmable L-to-F Converter, LUT Addressed by Either Period Count or Frequency Count)

Figure 13:
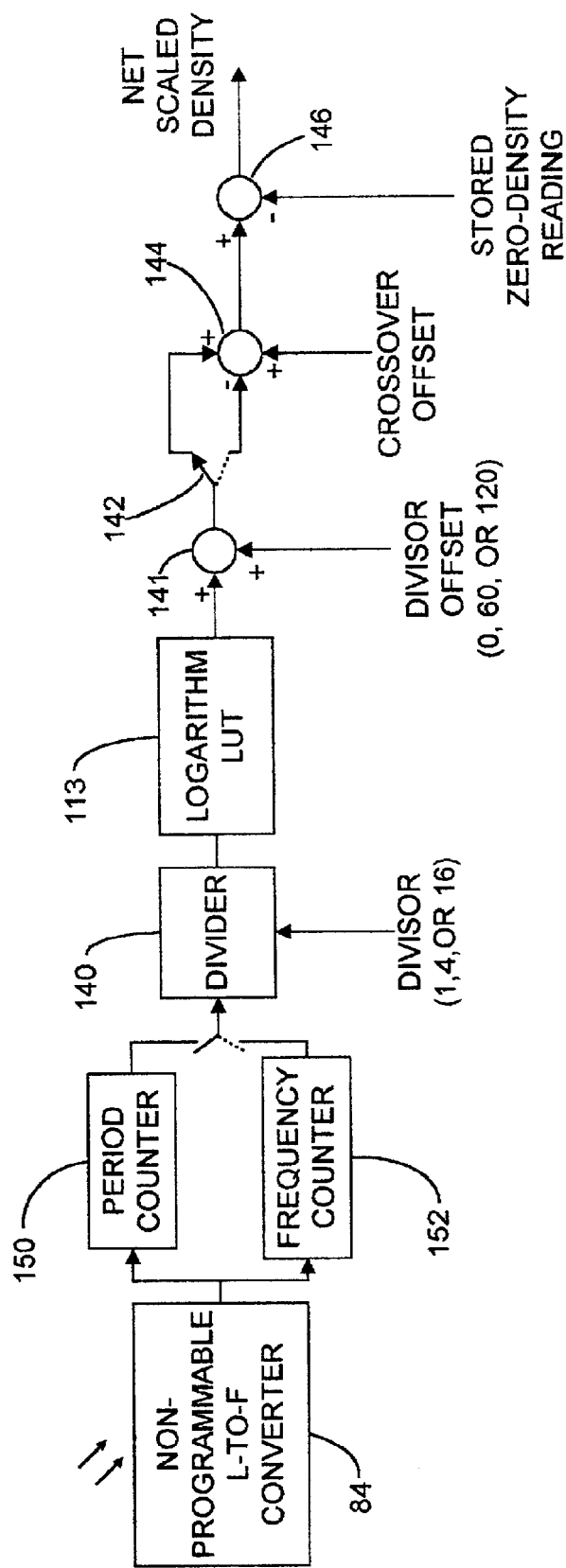
FIG. 13 is a block diagram of a densitometer according to the fifth preferred embodiment of the present invention.

As in the fourth preferred embodiment, the fifth also uses a non-programmable L-to-F converter, and the LUT pre-loaded as shown in the table of FIG. 12. However, the density measurement range is extended beyond the range of the fourth preferred embodiment by dealing with period counts less than 40, without loss of density resolution. A higher intensity light emitter is used such that low-density samples result in high intensity at the L-to-F converter, a high frequency output, and period counts less than 40. FIG. 13 depicts in block diagram form the transmitted or reflected light incident on a non-programmable L-to-F converter 84, and the subsequent counting and numerical processing. The subsequent functions depicted in FIG. 13 may be performed by separate coordinated components, or preferably combined in only one or a few components, such as a programmable microcontroller.

With continuing reference to FIG. 13, when a period counter 150 outputs a period count of at least 40, the period count is processed in a manner similar to the fourth preferred embodiment. The period count is divided, if necessary, in a divider 140 to obtain a value within the input range of a logarithm LUT 113. (Division by 1 is equivalent to no division.)

When period counter 150 outputs a period count less than 40, indicating that a low-density sample is being measured, a frequency counter 152 starts. Frequency counting continues for a predetermined fixed time interval sufficient to obtain a frequency count within the input range of logarithm LUT 113, with input count range of 41 to 291. If the light intensity is so great that the frequency count exceeds 291, the count is divided in divider 140 to obtain a divided frequency count within the input range of logarithm LUT 113. For the low-density samples, the frequency count, or divided frequency count, is used to address logarithm LUT 113, the same LUT addressed by the period count or divided period count for high-density samples. At a first node 141, the output of logarithm LUT 113 (with a range of 0 to 86) is increased by the offset associated with the divisor used.

The output of first node 141 is processed according to whether the LUT address was derived from a period count or a frequency count, and according to the divisor used. For period counting, density increases from a "crossover" value, with the increase proportional to the logarithm of the count. Conversely, for frequency counting, density decreases, with the decrease proportional to the logarithm of the count.

Therefore, for high densities and period counting, a "crossover" scaled density value is increased by the output of first node 141. A "sign" switch 142 directs the output of first node 141 to a positive sign at a second node 144, denoting addition to the crossover value.

For low densities and frequency counting, another "crossover" scaled density value is decreased by the output of node 141. "Sign" switch 142 directs the output of first node 141 to a negative sign at second node 144, denoting subtraction from the crossover value. For density measurement continuity across the period counting and frequency counting modes, the crossover value for frequency counting may need to be set higher than the crossover value for period counting, depending on the minimum frequency count. In this embodiment, the crossover values are the same only if the frequency counting time interval is set for a minimum frequency count of 41. The crossover value(s) are set high enough that a positive or zero difference remains after the subtraction at second node 144 or a zero-density sample.

FIG. 13 includes a final "zeroing" node 146, i.e., a subtraction of the stored raw scaled density value corresponding to a zero-density sample, or other reference sample, to obtain net scaled density.

VII. A General Logarithmic Converter Embodiment

The preferred embodiments disclosed hereinbefore are specifically for densitometers, wherein the circuit input signal is from a L-to-F converter sensitive to transmitted or reflected light and the output is a scaled density value. According to equation (1) density is defined as a negatively scaled logarithm of transmittance or reflectance. A densitometer LUT is pre-loaded accordingly. The densitometer circuits may be modified by inputting from a voltage-controlled oscillator (VCO), rather than from the L-to-F converter. Then, with a LUT pre-loaded for positively scaled logarithms of the input voltage, the circuit provides a scaled logarithmic conversion of a generic voltage input.

With the VCO at the input of the circuit, the frequency output is proportional to the voltage input, $V_{IN}$, rather than the light intensity, according to equation (2):

$$V_{IN}=kf \qquad \text{Equation (2)}$$

where f is the frequency of the VCO output, and k is a proportionality constant Since the VCO period, p, is the inverse of the frequency f, $$V_{IN}=k/p$$

Taking the logarithm of both sides of the equation gives, $$\log(V_{IN})=\log(k/p)$$

or, equivalently, $$\log(V_{IN})=-\log(p/k)$$

Thus, the logarithm of the input voltage $V_{IN}$ is a negatively scaled logarithm of the period count, as indicated in the table of FIG. 14 for the following example. Consider converting an analog input voltage $V_{IN}$ to dB gain, where dB gain is defined as 20 times the logarithm of ($V_{IN}$/10 mV), and $V_{IN}$ is in the range of 10 mV to 10 volts. The 60-dB range is to be integer scaled to the range of 0 to 255. $V_{IN}$ is connected to the input of the VCO, configured to output a frequency in the range of 1 kHz to 1000 kHz for $V_{IN}$ from 10 mV to 10 V. Divide-by ratios of N=1, 10, and 100 (binary codes 0, 1, and 2, respectively) are available to the divide-by logic, so that that the frequency after the divide-by-N function is in the range of 1 kHz to 10 kHz. A clock frequency is set to provide a period count in the range of 40 to 400, as in some of the preferred densitometer embodiments.

For $V_{IN}$=10 mV, the period count, p, is 400, N=1 (code 0), and the gain is 0 dB. The LUT address for p=400 and code=0 is pre-loaded with the zero-dB reference value. For $V_{IN}$=10 V, the period count is 40, N=100 (code=10 binary) and the gain is 60 dB. The LUT address for p=40 and code=2 is pre-loaded with the full-scale 8-bit value of 255, the integer scaled value for 60 dB. The other LUT entries are determined similarly as shown in the table of FIG. 14.

Figure 15:
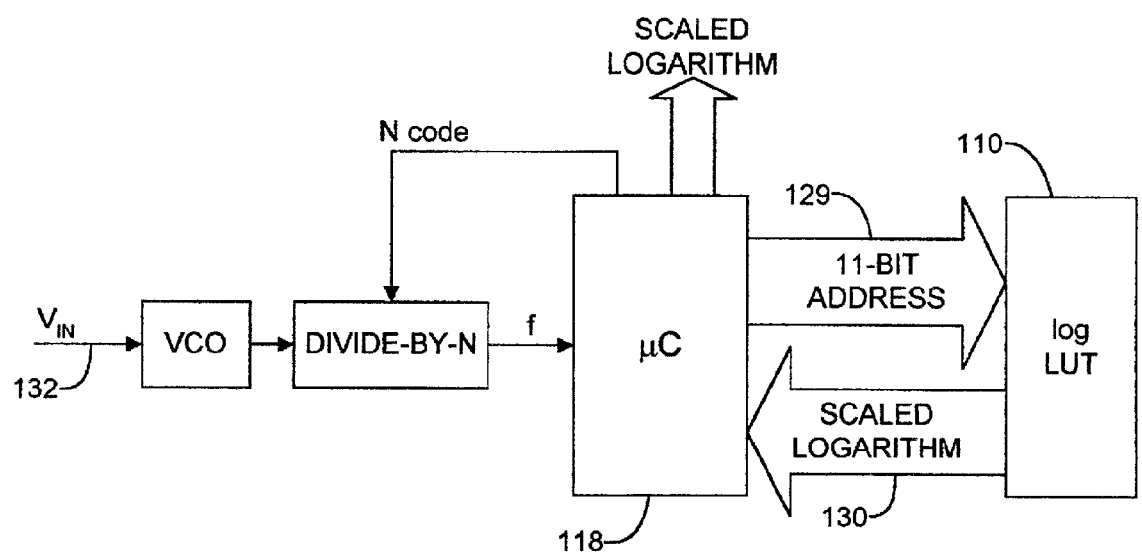
FIG. 15 is a block diagram for a general logarithmic converter circuit utilizing a voltage-to-frequency converter.

FIG. 15 shows a preferred embodiment for a logarithmic converter, where the source of input voltage signal 132 may be any sensor or sensor amplifier providing a voltage signal $V_{IN}$ within the operating range of the converter. Microcontroller 118 is programmed to set the divide-by ratio N to yield a period count in the range of 40 to 400. The microcontroller addresses a log LUT 110. An 11-bit LUT address 129 is formed by combining the 9-bit period count (40–400 decimal) with the 2-bit code for the divide-by ratio N (00, 01, or 10 binary). Log LUT 110 returns a scaled logarithm 130 of input voltage 132. The microcontroller may output the scaled logarithm value to any of a variety of devices according to the application, such as a display, a storage device, a host processor or network, or a D/A converter. Log LUT 110 is pre-loaded with the scaled logarithm values, where the scale factor preferably provides a full-scale digital output in response to a full-scale voltage input.

CONCLUSION, RAMIFICATIONS, AND SCOPE

An auto-ranging digital densitometer that includes a L-to-F converter, a period counter, and a LUT has been disclosed. The densitometer may also include L-to-F converter parameters dynamically programmed in real-time according to the sample density, and frequency counting. Presently preferred embodiments have been described to illustrate to advantages of simplicity and digital processing. Unlike many prior art densitometers, the measurement signals are processed more completely in digital form, no switching of analog signals is involved. Moreover, only a single lookup table is required, which may be relatively small in size, even for large density measurement ranges.

The logarithmic converter portion of the densitometer has been shown adaptable as a general digital logarithmic converter. Such a logarithmic converter is applicable in a variety of applications where there is need to convert an input to an output proportional to the logarithm of the input.

The invention has been described in detail with particular reference to preferred embodiments thereof, but it will be understood that variations and modifications can be effected within the spirit and scope of the invention. It should be especially recognized that densitometer embodiments of the present invention may be used in other applications besides electrophotographic copiers and printers.

What is claimed is:

1. A digital auto-ranging densitometer for determining the optical density of a test sample, said densitometer comprising:

a light-to-frequency converter circuit wherein at least one of the converter parameters from the group consisting of light sensitivity and frequency divide-by ratio, has a plurality of programmable values, and said light-to-frequency converter is adapted to produce a periodic signal having an output waveform with a frequency and period characteristic of the light intensity received from said test sample;

a clock outputting pulses equally spaced in time;

counter means to produce a period a period count of said clock pulses characteristic of the period of said output waveform; and converter parameter logic outputting a parameter code used to program said converter parameters, wherein said converter parameter values are changed in accordance with said count, until said count is within a predetermined range;

whereby said count in combination with said parameter code are characteristic of the optical density of said test sample.

2. A digital auto-ranging densitometer as set forth in claim 1, and further including a lookup table for storing optical density information, said lookup table containing, in each entry therein, at least the lower-order digits of a scaled density value corresponding to said converter parameter values and said period count, whereby said lookup table output in combination with said parameter code provide a digital measurement of said test sample density.

3. A digital auto-ranging densitometer as set forth in claim 2, wherein:

said period count is a subset of a plurality of address bits input to said lookup table;

said parameter code provides a remainder subset of said address bits input to said lookup table, such that said parameter code in combination with said counter provide a complete address to said lookup table; and said lookup table outputs all of the digits of said scaled density value corresponding to said light-to-frequency converter output and said parameter code.

4. A digital auto-ranging densitometer as set forth in claim 2, wherein:

said counter provides a complete set of address bits input to said lookup table;

said lookup table contains, in each entry therein, a low-order subset of digits of said scaled density value; and said parameter code denotes a high-order remainder subset of digits of said scaled density value, according to said converter parameter values such that said parameter code, in combination with said low-order subset, form a complete scaled density value.

5. A digital auto-ranging densitometer as set forth in claim 4, wherein:

said scaled density vales are represented in a base-B number system, where B is an integer between 2 and 20, inclusive;

said scaled density values are sealed such that said lookup table spans a scaled density increment of $B^K$, where K is an integer between 2 and 16, inclusive;

said lookup table outputs the K low-order base-B digits of said scaled density value; and said parameter code denoted the remaining high-order digits of said scaled density value.

6. A digital auto-ranging densitometer as set forth in claim 2, wherein:

said counter provides a complete set of address bits input to said lookup table;

said lookup table contains, in each entry therein, a low-order subset of digits of said scaled density value; and a high-order remainder subset of digits of said scaled density value are set according to said converter parameter values and said counter output, such that said high-order remainder subset, in combination with said low-order subset, form a complete scaled density value.

7. A digital auto-ranging densitometer as set forth in claim 2, wherein:

said light-to-frequency converter comprises an array of photodiodes, a programmable sensitivity control, said sensitivity control selecting one of a plurality of predetermined subsets of said array and summing the current output from said subset; a current-to-frequency converter circuit, and a programmable frequency divider; and a programmable microcontroller is adapted to provide said clock, said counter means, said converter parameter logic, and said lookup table, whereby the digital density measurement of said test sample is available from said microcontroller.

8. A digital auto-ranging densitometer as set forth in claim 2, wherein said light-to-frequency converter circuit comprises a photodiode, an amplifier circuit adapted to produce a voltage characteristic of the light flux incident on said photodiode, a voltage-controlled oscillator, and a programmable frequency divider.

9. A digital auto-ranging densitometer as set forth in claim 1, and further including a lookup table for storing optical density information, said lookup table containing, in each entry therein, offset scaled logarithm values of said period count, whereby said lookup table outputs a scaled density value of said test sample, with a density offset according to said parameter code.

10. A digital auto-ranging densitometer as set forth in claim 9, and further including means to remove said density offset, whereby a scaled density value is obtained for said test sample.

11. A process for determining the optical density of a test sample, said process comprising the steps of:

illuminating said test sample, with light impinging first upon said test sample, and thence from said test sample to a light-to-frequency converter;

producing a frequency output with frequency proportional to the intensity of the light incident on said light-to-frequency converter, where a proportionality constant is from a set of predetermined values;

measuring the period of said frequency output;

selecting said proportionality constant such that said measured period is within a predetermined range; and employing said selected proportionality constant and said measured period to obtain the optical density value of said test sample.

12. A digital auto-ranging densitometer for determining the optical density of a test sample, said densitometer comprising:

a light-to-frequency converter circuit adapted to produce a periodic signal having an output waveform with a frequency and period characteristic of the light intensity received from said test sample;

a clock outputting pulses equally spaced in time;

a period counter producing a period count of said clock pulses characteristic of the period of said output waveform; and a numerical divider, wherein said period count values are divided by a first divisor selected from a group of at least one predetermined divisors, producing a first quotient within a predetermined range;

whereby said first quotient in combination with said first divisor are characteristic of the optical density of said test sample.

13. A digital auto-ranging densitometer as set forth in claim 12, and further including a lookup table addressed according to said first quotient, and outputting an offset scaled logarithm value of said quotient, whereby said lookup table outputs a positively scaled density value of said test sample, with a first density offset according to said first divisor.

14. A digital auto-ranging densitometer as set forth in claim 13, and further including means to remove said first density offset, whereby a scaled density value is obtained for said test sample.

15. A digital auto-ranging densitometer as set forth in claim 13, and further including a frequency counter, operable when said period count is outside of and less than said predetermined range, producing a frequency count within said predetermined range and characteristic of the frequency of said output waveform, whereby said frequency count is characteristic of low density values of said test sample.

16. A digital auto-ranging densitometer as set forth in claim 15, and further including means to address said lookup table according to said frequency count, and to read the offset scaled logarithm of said frequency count from said lookup table, whereby said lookup table output is a negatively scaled density value of said test sample, with a second density offset.

17. A digital auto-ranging densitometer as set forth in claim 16, and further including means to remove said second density offset and negate the negative sign, whereby a scaled density value is obtained for relatively low density values of said test sample.

18. A digital auto-ranging densitometer as set forth in claim 13, and further including a frequency counter, operable when said period count is outside of and less than said predetermined range, producing a frequency count characteristic of the frequency of said output waveform, and wherein said numerical divider divides said frequency count by a second divisor selected from said group of at least one predetermined divisors, producing a second quotient within said predetermined range, whereby said frequency count, along with said second divisor, are characteristic of low density values of said test sample.

19. A digital auto-ranging densitometer as set forth in claim 18, and further including means to address said lookup table according to said second quotient, and to read the offset scaled logarithm of said second quotient from said lookup table, whereby said lookup table output is a negatively scaled density value of said test sample, with a second density offset according to said second divisor.

20. A digital auto-ranging densitometer as set forth in claim 19, and further including means to remove said second density offset and negate the negative sign, whereby a scaled density value is obtained for relatively low density values of said test sample.

21. A process for determining the optical density of a test sample, said process comprising the steps of:

illuminating said test sample, with light impinging first upon said test sample, and thence from said test sample to a light-to-frequency converter;

producing a frequency output with frequency proportional to the intensity of the light incident on said light-to-frequency converter;

measuring the period of said frequency output in terms of a period count, said period count being at least within a predetermined range;

dividing said period count by a divisor selected from a group of at least one predetermined divisors, to yield a period quotient within said predetermined range;

entering a lookup table, addressed according to said period quotient;

reading an offset scaled logarithm value from said lookup table; and employing said offset scaled logarithm value, along with said divisor, to obtain a scaled density value of said test sample.

22. A process for determining the optical density of a test sample, said process comprising the steps of:

illuminating said test sample, with light impinging first upon said test sample, and thence from said test sample to a light-to-frequency converter;

producing a frequency output with frequency proportional to the intensity of the light incident on said light-to-frequency converter;

measuring the period of said frequency output in terms of a period count;

dividing said period count by a divisor selected from a group of at least one predetermined divisors, when said period count is at least within a predetermined range, to yield a period quotient within said predetermined range;

measuring the frequency of said frequency output, obtaining a frequency count within said predetermined range, when said period count is outside of and less than said predetermined range;

entering a lookup table, addressed according to said period quotient when said period count is at least within said predetermined range, and according to said frequency count when said period count is less than said predetermined range;

reading an offset scaled logarithm value from said lookup table;

employing said offset scaled logarithm value to obtain a scaled density value of said test sample when said period count is less than said predetermined range; and employing said offset scaled logarithm value, along with said divisor, to obtain a scaled density value of said test sample when said period count is at least within said predetermined range.

23. A process for determining the optical density of a test sample, said process comprising the steps of:

illuminating said test sample, with light impinging first upon said test sample, and thence from said test sample to a light-to-frequency converter;

producing a frequency output with frequency proportional to the intensity of the light incident on said light-to-frequency converter;

measuring the period of said frequency output in terms of a period count;

dividing said period count by a first divisor selected from a group of at least one predetermined divisors, when said period count is at least within a predetermined range, to yield a period quotient within said predetermined range;

measuring the frequency of said frequency output, obtaining a frequency count at least within said predetermined range, when said period count is outside of and less than said predetermined range;

dividing said frequency count by a second divisor from said group of at least one predetermined divisors, when said period count is outside and less than said predetermined range, to yield a frequency quotient within said predetermined range;

entering a lookup table, addressed according to said period quotient when said period count is at least within said predetermined range, and according to said frequency quotient when said period count is less than said predetermined range;

reading an offset scaled logarithm value from said lookup table;

employing said offset scaled logarithm value, along with said second divisor, to obtain a scaled density value of said test sample when said period count is less than said predetermined range; and employing said offset scaled logarithm value, along with said first divisor, to obtain a scaled density value of said test sample when said period count is at least within said predetermined range.

24. A digital logarithm converter comprising:

a voltage-controlled oscillator with a programmable frequency divide-by ratio, with a plurality of programmable values, and adapted to produce a periodic signal having an output waveform with a frequency and period characteristic of an input voltage;

a clock outputting pulses equally spaced in time;

counter means to produce a period count of said clock pulses characteristic of the period of said output waveform; and divide-by logic outputting a code used to program said divide-by ratio, wherein said divide-by ratio is changed in accordance with said count, until said count is within a predetermined range;

whereby said count in combination with said divide-by ratio are characteristic of the logarithm of said input voltage.

25. A digital logarithmic converter as set forth in claim 24, and further including a lookup table for storing logarithm information, said lookup table containing, in each entry therein, at least the lower-order digits of a scaled logarithm value corresponding to said code and said period count, whereby said lookup table output in combination with said code provide a digital measurement of the logarithm of said input voltage.

26. A digital logarithmic converter as set forth in claim 25, wherein:

said period count is a subset of a plurality of address bits input to said lookup table;

said code provides a remainder subset of said address bits input to said lookup table, such that said code in combination with said counter provide a complete address to said lookup table; and said lookup table outputs all of the digits of said scaled logarithm value corresponding to said period count and said code.

27. A digital logarithmic converter as set further in claim 25, wherein:

said counter provides a complete set of address bits input to said lookup table;

said lookup table contains, in each entry therein, a low-order subset of digits of said scaled logarithm value; and said code denotes a high-order remainder subset of digits of said scaled logarithm value, according to said divide-by ratio, such that said code, in combination with said low-order subset, form a complete scaled logarithm value.

28. A digital logarithmic converter as set forth in claim 27, wherein:

said scaled logarithm values are represented in a base-B number system, where B is an integer between 2 and 20, inclusive;

said scaled logarithm values are scaled such that said lookup table spans a scaled logarithm increment of $B^K$, where K is an integer between 2 and 16, inclusive;

said lookup table outputs the K low-order base-B digits of said scaled logarithm value; and said code denotes the remaining high-order digits of said scaled logarithm value.

29. A digital logarithmic converter as set forth in claim 25, wherein:

said counter provides a complete set of address bits input to said lookup table;

said lookup table contains, in each entry therein, a low-order subset of digits of said scaled logarithm value; and a high-order remainder subset of digits of said scaled logarithm value are set according to said divide-by ratio and said counter output, such that said high-order remainder subset, in combination with sid low-order subset, form a complete scaled logarithm value.

30. A digital logarithmic converter as set forth in claim 24, and further including a lookup table for storing logarithm information, said lookup table containing, in each entry therein, offset scaled logarithm values of said period count, whereby said lookup table outputs a scaled logarithm value of said input voltage, with an offset according to said code.

31. A digital logarithmic converter as set forth in claim 30, and further including means to remove said offset, whereby a scaled logarithm value is obtained for said input voltage.

32. A digital logarithmic converter for determining the logarithm of an input voltage, comprising:

a voltage-controlled oscillator adapted to produce a periodic signal having an output waveform with a frequency and period characteristic of an input voltage;

a clock outputting pulses equally spaced in time;

a period counter producing a period count of said clock pulses characteristic of the period of said output waveform; and a numerical divider, wherein said period count values are divided by a first divisor selected from a group of at least one predetermined divisors, producing a first quotient within a predetermined range;

whereby said first quotient in combination with said first divisor are characteristic of the logarithm of said input voltage.

33. A digital logarithmic converter as set forth in claim 32, and further including a lookup table addressed according to said first quotient, and outputting an offset scaled logarithm value of said quotient, whereby said lookup table outputs a positively scaled logarithm value of said input voltage, with a first offset according to said first divisor.

34. A digital logarithmic converter as set forth in claim 33, and further including means to remove said first offset, whereby a scaled logarithm value is obtained for said input voltage.

35. A digital logarithmic converter as set forth in claim 33, and further including a frequency counter, operable when said period count is outside of and less than said predetermined range, producing a frequency count within said predetermined range and characteristic of the frequency of said output waveform, whereby said frequency count is characteristic of small values of said input voltage.

36. A digital logarithmic converter as set forth in claim 35, and further including means to address said lookup table according to said frequency count, and to read the offset scaled logarithm of said frequency count from said lookup table, whereby said lookup table output is a negatively scaled logarithm value of said input voltage, with a second offset.

37. A digital logarithmic converter as set forth in claim 36, and further including means to remove said second offset and negate the negative sign, whereby a scaled logarithm value is obtained for relatively small values of said input voltage.

38. A digital logarithmic converter as set forth in claim 33, and further including a frequency counter, operable when said period count is outside of and less than said predetermined range, producing a frequency count characteristic of the frequency of said output waveform, and wherein said numerical divider divides said frequency count by a second divisor selected from said group of at least one predetermined divisors, producing a second quotient within said predetermined range, whereby said frequency count, along with said second divisor, are characteristic of small values of said input voltage.

39. A digital logarithmic converter as set forth in claim 38, and further including means to address said lookup table according to said second quotient, and to read the offset scaled logarithm of said second quotient from said lookup table, whereby said lookup table output is a negatively scaled logarithm value of said input voltage, with a second offset according to said second divisor.

40. A digital logarithmic converter as set forth in claim 39, and further including means to remove said second offset and negate the negative sign, whereby a scaled logarithm value is obtained for relatively small values of said input voltage.

* * * * *

UNITED STATES PATENT AND TRADEMARK OFFICE
CERTIFICATE OF CORRECTION

PATENT NO. : 6,791,485 B1
APPLICATION NO. : 10/095166
DATED : September 14, 2004
INVENTOR(S) : Allen J. Rushing It is certified that error appears in the above-identified patent and that said Letters Patent is hereby corrected as shown below:

Title Page, Section Entitled, "Related U.S. Application Data",
Delete ", and a continuation-in-part of application No. 09/873,465, filed on Jun. 4, 2001, now Pat. No. 6,671,052."

Column 1,
Lines 12-14, delete ", and is a CIP of Ser. No. 09/873,465 filed Jun. 4, 2001 U.S. Pat. No. 6,671,052."

Signed and Sealed this

Twelfth Day of August, 2008

JON W. DUDAS
*Director of the United States Patent and Trademark Office*